(12) United States Patent
Kligman et al.

(10) Patent No.: US 6,228,887 B1
(45) Date of Patent: *May 8, 2001

(54) METHOD OF TREATING SKIN DISORDERS WITH HIGH-STRENGTH RETINOIDS

(76) Inventors: Douglas E. Kligman; Albert M. Kligman, both of 151 E. Tenth St., Conshohocken, PA (US) 19428

( * ) Notice: Subject to any disclaimer, the term of this patent is extended or adjusted under 35 U.S.C. 154(b) by 0 days.

This patent is subject to a terminal disclaimer.

(21) Appl. No.: 09/567,792

(22) Filed: May 9, 2000

Related U.S. Application Data

(63) Continuation of application No. PCT/US98/09440, filed on May 11, 1998, and a continuation-in-part of application No. 09/071,017, filed on Dec. 28, 1999, now Pat. No. 6,008,254.
(60) Provisional application No. 60/046,070, filed on May 9, 1997.

(51) Int. Cl.$^7$ ............................. A61K 31/19; A61K 31/07
(52) U.S. Cl. ............................................ 514/570; 514/725
(58) Field of Search ..................................... 514/570, 725

(56) References Cited

U.S. PATENT DOCUMENTS

| | | |
|---|---|---|
| 3,729,568 | 4/1973 | Kligman . |
| 4,603,146 | 7/1986 | Kligman . |
| 4,888,342 | 12/1989 | Kligman . |
| 5,643,584 | 7/1997 | Farng et al. . |
| 6,008,254 | * 12/1999 | Kligman et al. ..................... 514/570 |

FOREIGN PATENT DOCUMENTS

| | | |
|---|---|---|
| 0 379 367 A2 | 7/1990 | (EP) . |
| 0 415 766 A2 | 3/1991 | (EP) . |
| WO 92/15290 | 9/1992 | (WO) . |
| WO 92/15293 | 9/1992 | (WO) . |
| WO 93/15740 | 8/1993 | (WO) . |

OTHER PUBLICATIONS

Griffiths, C.E., et al., "Topical Tretinoin (Retinoic Acid) Improves Melasma. A Vehicle–Controlled, Clinical Trail," *British Journal of Dermatology*, 129(4): 415–421 (1993).

Vademecum Internacional, 34th Edition, *Medicom, S.A.*, Madrid XP002077890, "Dermojuventus," p. 497 (1993).

Marks, Ronald, et al., "Techniques for Assessing the Activity of Topically Applied Retinoids," *Journal of the American Academy of Dermatology*, 15(4): 810–816 (1986).

Thomas, Jesse R., III, et al., "The Therapeutic Uses of Topical Vitamin A Acid," *Journal of the American Academy of Dermatology*, 4(5): 505–516 (1981).

Kaidbey, K.H., et al., "Treatment of Psoriasis with Topically Applied Tretinoin and Steroid Ointment," *Arch. Dermatol.*, 111(8): 1001–1003 (1975).

*Martindale: The Extra Pharmacopoeia*, 28th Ed., p. 508 (1982).

* cited by examiner

*Primary Examiner*—Raymond Henley, III
(74) *Attorney, Agent, or Firm*—Akin, Gump, Strauss, Hauer & Feld, L.L.P.

(57) ABSTRACT

Various skin disorders, excluding acne are treated by topical application to the skin of a retinoid-composition including a retinoid in a dermatologically acceptable vehicle at such a concentration and applied in such a way as to induce desquamation of the skin to ameliorate the disorder. Preferably, the compositions contain greater than 0.1 weight percent tretinoin, and more preferably at least 0.2 weight percent tretinoin. The vehicle is preferably a solvent for the retinoid such as an alcohol/glycol or hydroalcoholic vehicle, but it is also possible to apply the retinoid in a non-solvent vehicle such as emulsifying or suspending the retinoid in a cream, dressing, gel, ointment or liquid polymer, with or without penetration enhancers. The treatment achieves rapid amelioration of skin disorders such as photodamaged skin, hyperpigmentation, rosacea, premalignant cancers including actinic keratoses, wrinkles, superficial scarring, epidermal atrophy and atypia, and keratosis pilaris, by daily or every other day application for about one to two months. Thereafter, the high strength applications may be tapered off, and the treated skin maintained with more conventional lower concentration compositions.

11 Claims, No Drawings

METHOD OF TREATING SKIN DISORDERS WITH HIGH-STRENGTH RETINOIDS

CROSS-REFERENCE TO RELATED APPLICATION

This application is a continuation of International Application PCT/US98/09440, filed May 11, 1998 the disclosure of which is incorporated herein by reference. This international application is also a continuation-in-part of Non-Provisional Application Ser. No. 09/071,017, filed Dec. 28, 1999, issued as U.S. Pat. No. 6,008,254 which was based upon Provisional Application Ser. No. 60/046,070, filed May 9, 1997 now abandoned.

BACKGROUND OF THE INVENTION

The invention is directed to the treatment of various skin disorders with high-strength tretinoin (also known as vitamin A acid or all-trans retinoic acid) or other retinoids. More particularly, the invention is directed to the treatment of skin disorders, especially of human facial skin, with amounts of retinoid sufficient to ameliorate the disorder.

Caucasians who have had a good deal of sun exposure in childhood will show the following gross cutaneous alternations in adult life: wrinkling, leatheriness, yellowing, looseness, roughness, dryness, mottling (hyperpigmentation) and various premalignant growths (often subclinical). These changes are most prominent in light-skinned persons who burn easily and tan poorly. The baleful effects of sunlight are cumulative, increasing with time and often referred to as "photoaging". Although the anatomic degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness, loss of elasticity are very late changes.

Retinoids (e.g., Vitamin A and its derivatives) are substances which are known to have a broad spectrum of biological activity. More specifically, these substances affect cell growth, differentiation and proliferation. Retinoids affect the differentiation, maintenance, and proliferation of many types of cells whether they are of ectodermal, endodermal or mesodermal origin; whether they are epithelial, fibroblastic or mesenchymal; or whether they are neoplastic, preneoplastic or non-neoplastic. Retinoids have found clinical utility in the treatment of severe cystic acne, psoriasis, and other disorders of keratinization. Possible uses of retinoids are being explored in the prophylaxis and treatment of cancer. For a recent review of developments in the uses of retinoids, see Orfanos et al., "Current Use and Future Potential Role of Retinoids in Dermatology," *Drugs* 53:358–380 (March 1997).

Other older reviews of the uses of retinoids in research and clinical medicine can be found in the publication of a symposium held in Geneva: J. H Saurat, Editor, "Retinoids: New Trends in Research and Therapy", Karger Publishing Co. (1985); Pawson, B. A. et al., "Retinoids at the Threshold: Their Biological Significance and Therapeutic Potential", *Journal of Medicinal Chemistry* 25: 1269–1277 (1982); and Thomas, J. R., et al., "The Therapeutic Uses of Topical Tretinoin", *Journal of American Academy of Dermatology* 4:505–516 (1981).

It is known to use tretinoin topically for treatment of acne as set forth in U.S. Pat. No. 3,729,568 of A. M. Kligman. That patent discloses the treatment of acne with tretinoin in alcohol/glycol vehicles at concentrations sufficient to cause irritation including inflammation and peeling, such concentrations ranging as high as 0.5 weight percent, preferably 0.05 to 0.25 weight percent.

U.S. Pat. Nos. 4,603,146; 4,877,805 and 4,888,342 of A. M. Kligman disclose long term methods for treating sun-damaged human skin topically with low concentrations of tretinoin and other retinoids in an emollient vehicle, such amounts of retinoids being essentially non-irritating to the skin. This treatment requires periodic applications for several months before improvement is achieved, and this factor often leads to the treated individual discontinuing treatment before positive results are obtained.

SUMMARY OF THE INVENTION

According to the method of the present invention, skin disorders, excluding acne, are treated by topical application to the affected skin of a retinoid composition comprising a retinoid in a dermatologically acceptable vehicle, wherein the concentration of the retinoid in the composition and the topical application are effective to induce desquamation of the skin to ameliorate the disorder. The concentration of the preferred retinoid, tretinoin, in the composition is preferably greater than 0.1 weight percent, and more preferably at least about 0.2 weight percent tretinoin.

The vehicle may be a solvent for the retinoid, such as ethanol, isopropanol, acetone, diethyl ether, propylene gylcol, polyethylene glycol and hydroalcoholic solvents, with mixtures of ethanol and polyethylene glycol being preferred. Is also possible to emulsify or suspend the retinoid in non-solvent vehicles, such as creams, dressings, gels, ointments and liquid polymers. The composition may also contain a penetration enhancing agent.

The retinoid-containing composition may be applied to facial skin, forearms, hands, upper chest, upper back, neck and scalp, in particular, or wherever the skin disorder is externally visible and of concern to the patient being treated. The composition is initially applied to the skin on the average of from about every day up to about one month to every other day for up to about two months. After the initial application regimen, the treatment may be tapered off to a lower concentration composition containing a retinoid for maintenance of the treated skin.

In its broadest aspects, the treatment of the present invention may be applied to skin affected with various disorders, including photodamaged skin, hyperpigmentation, rosacea, premalignant skin cancers including actinic keratoses, wrinkles, superficial scarring, epidermal atrophy and atypia, and keratosis pilaris. In one preferred embodiment, the present invention is directed to treatment of aging changes in the skin by topical application of high-strength retinoid in an alcoholic carrier or other suitable vehicle. Photoaging skin changes (sun damage) first become evident clinically in young to middle aged adults and are most evident in exposed portions of the body, particularly facial skin. Certain anatomic alterations associated with photoaging can be treated in a relatively short time using this invention, resulting in improvement in the appearance of the skin. Such skin abnormalities are corrected and modified to the extent that the structure and function of the skin acquires the characteristics of younger (undamaged) skin. This invention is particularly useful for providing rapid improvement in the treated skin, and such improvement can be maintained afterwards through conventional skin treatment programs.

In another preferred embodiment, the present invention is directed to the treatment of actinic keratoses (also known as solar keratoses). These are premalignancies which start in the basal cells of the epidermis, which left untreated may work down into the dermis and become malignancies. The treatment of actinic keratoses according to the present invention may require or benefit from twice daily application of the retinoid at the start of treatment, particularly for actinic keratoses of the hands, arms and other parts of the body.

DETAILED DESCRIPTION OF THE INVENTION

A retinoid is used as the active ingredient in this invention. A preferred retinoid is tretinoin, also known as vitamin A acid or all-trans retinoic acid.

Retinoids have been defined narrowly as comprising simply vitamin A (retinol) and its derivatives, such as vitamin A aldehyde (retinal), vitamin A acid (retinoic acid), comprising the so called natural retinoids. However, subsequent research has resulted in a much larger class of chemical compounds that are termed retinoids due to their biological similarity to vitamin A and its derivatives. Thus, there are now a number of so-called retinoic acid receptor (RAR)-specific retinoids which have been found to react with retinoid receptors despite having quite different structures from Vitamin A.

Compounds useful in the present invention include all natural and/or synthetic analogues of vitamin A or retinol-like compounds, as well as RAR-specific retinoids, which possess the biological activity of vitamin A in the skin, such as the control of epithelial cell differentiation of keratinocytes in the epidermis and/or stimulation of fibroplasia or new collagen synthesis in the dermis among other effects. Accordingly, as used herein for purposes of the present invention, the term "retinoid" will be understood to include any of the foregoing compounds. Examples of suitable retinoids for use in the present invention which are presently commercially available or in clinical trials include: 13-cis retinoic acid (isotretinoin), 9-cis retinoic acid, tazarotene (an acetylinic or RAR specific retinoid from Allergan, Inc.), and adapalene (a naphthoic acid derivative from Galderma Laboratories, Inc.)

There are preferably no other active ingredients in the retinoid compositions used in this invention, particularly no other active ingredients or components with known activity in treating skin disorders by chemical skin peeling, e.g., alpha hydroxy acids, salicylic acid, trichloroacetic acid, resorcinol and the like. However, steroids or other drugs may be used concurrently to offset side affects, where present or appropriate.

The retinoid used in this invention is applied to the skin being treated in a composition or formulation suitable for topical application, i.e., directly dabbing or spreading on the epidermis. The retinoid composition includes a carrier or vehicle, preferably a liquid vehicle that is a solvent for the retinoid and is dermatologically acceptable. The term "dermatologically acceptable" means suitable for use in contact with skin tissue without undue toxicity, incompatibility, instability or adverse reaction with the skin or the active ingredient, e.g. tretinoin.

Tretinoin and other retinoids are substantially insoluble in aqueous vehicles. Therefore, organic solvent vehicles are preferred as the liquid carrier. Alcoholic vehicles such as ethanol and isopropanol are preferred, with ethanol being most preferred. Other suitable solvent vehicles to form a solution of a retinoid include, for example, acetone, diethyl ether, liquid glycols or glycol derivatives, and hydroalcoholic vehicles.

The solvent vehicle may also be a mixture of such components. A particularly suitable solvent vehicle carrier for tretinoin comprises an alcohol selected from the group consisting of ethanol and isopropanol and a suitable liquid glycol or glycol derivative. Examples of suitable glycols are liquid polyethylene glycols, such as polyethylene glycol 400, propylene glycol and liquid polypropylene glycols. Of these, polyethylene glycols and propylene glycols are preferred. Examples of suitable liquid glycol derivatives include ethylene glycol ethers, such as mono-, di- and triethylene glycol monomethyl ethers and mono- di- and triethylene glycol monoethyl ethers.

A preferred solvent vehicle for tretinoin comprises from about 20 to 80% by weight of ethanol or isopropanol and the balance being a liquid glycol, preferably polyethylene glycol.

Instead of a solvent carrier, the retinoid may be suspended or emulsified in a non-solvent vehicle, such as any of various formulations known or available in the art, including creams, dressings, gels, ointments and liquid polymers. Whatever the vehicle or carrier selected for the retinoid, it is important that it be one which promotes good contact with and penetration into the skin, not only into the epidermis, but preferably also into the dermis. Thus, vehicles are preferred which drive the highest concentration across the stratum corneum as possible. Alcoholic vehicles are particularly useful in this regard, whereas polymers, sponges and other vehicles which may retard or sequester release of the active agent are not preferred. Although tretinoin, for example, is in itself a good penetration enhancer, additional penetration enhancing agents may be helpful in some circumstances, and such agents are generally known to those of ordinary skill in the art.

The retinoid concentration in the vehicle is such that the topical application will cause desquamation of the skin, including superficial and/or subclinical peeling. In the case of tretinoin the concentration is preferably greater than 0.1% by weight, e.g., at least about 0.12% by weight, and more preferably at least about 0.2% by weight tretinoin in the vehicle. Concentrations greater than about 0.3 to 0.5% by weight are unnecessary and not preferred. A particularly preferred formulation contains about 0.25% by weight tretinoin in a liquid carrier comprising ethanol and polyethylene glycol 400. These concentrations of tretinoin are percent by weight based on the total weight of the formulation. Such concentration are referred to herein as "high-strength" in contrast to lower strength concentrations, i.e. up to about 0.1% by weight, which for most people will not cause intensive inflammation and/or peeling. In the case of other retinoids, the concentration sufficient to cause desquamation may be different from that of tretinoin, but can be determined by one skilled in the art without undue experimentation.

The topical retinoid formulations of this invention are preferably solutions in which the retinoid is completely dissolved. The formulations may also contain other dermatologically acceptable adjuvants, such as antioxidants or other formulation stabilizers that provide increased shelf life, thickening agents, and other conventional skin care formulation additives, e.g., sunscreens or sun blocks.

The retinoid composition of this invention is initially applied to the skin to be treated either daily, or every other day or every third day, with single applications every day or every second day being preferred. For treatment of facial skin, the composition is applied to the entire face, i.e., the forehead, cheeks, around crows feet areas, the lower eyelids, the nose, the upper lip and the chin. Other areas of the skin, such as dorsal forearms, hands, upper chest, upper back, neck, and scalp, may be treated in the same way as facial skin. Preferably, the composition is applied at night prior to the individual going to bed. Application of the retinoid composition may be made by conventional means, e.g., a cotton-tipped applicator, a gauze pad, or the like. After each application of the retinoid composition, the composition is allowed to dry on the skin by at least partial evaporation of the vehicle.

In the case of the treatment of actinic keratoses, it may be desired to apply the retinoid composition twice a day, in a manner similar to the conventional treatment of actinic keratoses with 5-fluorouracil. This is particularly the case with treatment of thicker hypertrophic actinic keratoses or with treatment of the forearms, hands and other parts of the body which may be more tolerant to irritation than the face, and may require more intensive treatment to effect desquamation. Further, treatment of actinic keratoses and other skin disorders besides photoaging may be by spot application to visible lesions or affected areas of the skin, instead of by general application to the skin.

During the initial 1–2 weeks of treatment, the high concentration of retinoid present in the composition results in an intensive inflammation or irritation to the skin that is nevertheless generally at an acceptable or tolerable level for most individuals, when the preferred application rate of every night or every other night is used. The skin irritation is observable as a flushing or diffuse reddening of the skin on which the retinoid formulation is applied. For most individuals, erythema and desquamation (peeling) develop in about 7–10 days after initiation of treatment and subside in about another 7–10 days. Thus, in most cases, depending on the individual treated and the concentration and/or frequency of application, a superficial chemical skin peel, as well as subclinical peeling, is effected by the high-strength retinoid treatment. After the initial peeling, the patient's skin accommodates to the high dose, probably due to down-regulation of the cells, so that further treatment is more easily tolerated.

If desired, a bland moisturizer may be used during the time of peeling, typically over the first two weeks of treatment, which makes the irritation and peeling that occurs during this period more tolerable to the treated individuals. For individuals with more sensitivity to the irritating sensation, application of the retinoid tretinoin composition may be made every three days instead of the preferred application every one or two days. For individuals with more extensive photodamage, particularly elderly individuals who typically have a dampened inflammatory response, the tretinoin composition may be applied daily, rather than every other day.

After the initial two to three weeks of treatment, the retinoid composition may be applied daily since the irritation response subsides for most treated individuals. The treatment is continued for a total period of time of about 1–2 months, preferably about 4–6 weeks. Generally after about 3–4 weeks, the treated individuals report significant improvement in the treated skin such as smoothing, more suppleness and softness to the skin, diminution of fine lines, decreased sallowness (yellow color) and more vascularity as evidenced by a rosier glow to the skin. These results may be corroborated by photographic analysis of the treated individual both pre- and post-treatment. Treated individuals typically find that makeup (foundation) is easier to apply since the dry surface of photodamaged skin has been eliminated and replaced with an increase in skin moisturization, e.g., as measured by conductance using a Novameter.

Examination of skin biopsy specimens by histology confirms that reversal of photodamage is seen early in the course of the treatment of this invention. Such skin improvement includes normalization of epidermal atypia, thinning of the stratum corneum, acanthosis of the stratum germinativum, increased rete ridge patterns, dispersal of pigment granules, increased collagen fiber synthesis in the papillary dermis, and increase vascularity, as well as improved skin elasticity and increased skin moisturization.

After completion of the treatment of photoaging according to the method of this invention, the improvement in skin condition and appearance may be maintained by use of conventional skin treatment protocols, e.g., treatment with low strength (0.05%) tretinoin emollient creams, or other retinoid compositions, such as retinol or isotretinoin formulations.

The present invention is not only useful for treating individuals with photodamaged or photoaged skin, but also may be used with individuals who have other skin disorders including rosacea, hyperpigmentation (melasma), premalignant skin cancers (including actinic keratoses), wrinkles, superficial scarring, epidermal atrophy and/or atypia, and keratosis pilaris.

The retinoid treatment of this invention is surprisingly well tolerated by individuals being treated and results in rapid improvement of skin condition and appearance. Fine lines and wrinkles are reduced, blotchiness is diminished, and rough scaling is replaced by a smooth skin surface. Increased skin firmness is evident by palpation, and this may be confirmed by physical measurements of elasticity. The increased smoothness and improved texture of the skin that results may be confirmed by Silflo replicas. The increased hygroscopicity and water holding capacity in the stratum corneum of the treated skin may be confirmed by impedance measurements using a Novameter. The cosmetic benefits that result from the treatment method of this invention are noteworthy for treated individuals whose skin initially exhibits fine line wrinkles, mottled hyperpigmentation, skin roughness, and other symptoms associated with photoaging and photodamage.

In the case of the treatment of premalignancies such as actinic keratoses, it is believed that retinoids can drive apoptosis. Thus, while applicants do not wish to be bound by any particular theory, it is believed that the noraml killing off of cells that are aberrant (apoptosis) is interrupted by the premalignancies, so that the aberrant cells continue to divide and multiply. Retinoids appear to have the ability to stop the aberrant cell division by reinstituting a sort of apoptosis program so that the premalignant cells are killed off.

The invention will now be illustrated in more detail by reference to the following specific, non-limiting examples:

EXAMPLES 1 and 2

Two studies were performed on groups of women ranging in age from approximately 35 to 60 years of age who exhibited signs of photodamage. The women were screened by dermatologists and enrolled in the study provided they met commonly accepted criteria for photoaging. Subjects were instructed on how to apply a solution of 0.25% tretinoin (tretinoin), in a 50:50 mixture of 95% ethanol/polyethylene glycol 400 vehicle, to the skin. These applications were performed by the subjects at home following a demonstration at the laboratory. Application was performed using cotton tip applicators from which the solution was applied to the entire face. The solution was applied at night after cleansing the face with a mild cleanser.

Two groups of women were studied, in which the first consisted of 16 women, and the second group consisted of 24 women. Several women were unable to make all scheduled visits and were therefore not included in the data presented herein. None of the women dropped out of the study due to irritation, and in fact the regimen was well tolerated. Initially, the solution was applied every other night. The frequency of application was thereafter increased to every night as they became acclimatized to the solution, typically about two weeks after the treatment was initiated. There is a delay of several days before peeling and erythema begin, and this continues for approximately 10 to 14 days, after which, in most subjects the peeling stops. Treatment was continued for a total of 4 to 6 weeks for the women in each group.

In Table 1 there is provided an assessment of two dermatologists of photographs taken of 33 of the subjects at both pre- and post-treatment. An overall clinical impression (Global Improvement) takes into account a variety of skin parameters of photoaging including, fine wrinkling, coarse wrinkling, roughness, sallowness (which refers to the yellow color due to solar elastosis), looseness, and pigment. Approximately 85% of the treated subjects had global improvement. Fine line improvement was seen in approximately 75% of the treated subjects; and a decrease in hyperpigmentation was seen in approximately 15% of the subjects (some of the study subjects did not exhibit significant hyperpigmentation when enrolled, and this provides an explanation as to why this number in Table 1 is believed to be artificially low).

TABLE 1

FACIAL SKIN IMPROVEMENT AFTER 1 MONTH
Number of subjects: 33

|  | 1st dermatologist | 2nd dermatologist |
|---|---|---|
| global improvement | 28/33 | 28/33 |
| fineline improvement | 23/33 | 26/33 |
| decreased hyperpigmentation | 5/33* | 5/33* |

*only 5 subjects had significant hyperpigmentation to start

Subjective assessments (self assessment by the study subjects) were obtained and demonstrated that most of the subjects were pleased and almost all of the subjects felt that their skin was smoother and softer, as compared with no treatment. Only 1 out of 40 subjects reported no change in her facial skin following treatment. In each of the subjects, a rosy glow was observed after treatment, as compared with a yellow sallow appearance to the skin prior to treatment. The post-treatment skin of the subjects also exhibited more turgor to the touch and thus was less loose than prior to treatment. The post-treatment skin appeared shinier, and this was attributable to improved surface smoothness which increases light reflectance.

Punch biopsies were obtained from the cheek of several subjects and processed for histology with hematoxylin eosin and special stains. Compared with pretreatment biopsies, the biopsies exhibited typical changes, as follows.

In the epidermis this includes: a thickening of the overall epidermal thickness due to acanthosis of the stratum germanitivum; thinning of the stratum corneum; an increased rete ridge pattern and dispersal of basal layer pigment granules; and atypia is normalized and atrophy and dysplasia were corrected.

In the dermis this includes: stimulation of fibroblast proliferation and metabolism with resulting increased collagen synthesis and a papillary dermal grenz zone found epidermally; new blood vessel formation with well-developed adventitial cells; and special stains reveal that solar elastosis is less severe after treatment, with some elastic fibers becoming clearly detectable instead of in amorphous pattern.

The observed histologic changes are achieved in the present invention within a relatively short time, a few weeks, after initiation of he treatment, as contrasted with lower strength Retin-A regimens in which such changes are observed only after many months of treatment.

Table 2 comprises primary data obtained from subjects who were analyzed by Silflo replica analysis for fine lines and wrinkles pre- and post-treatment with 0.25% tretinoin as described above. Computer analysis reveals a statistically significant reduction in total line length in all subjects. This correlates with the clinical assessments and the photographic assessments of the study subjects. Skin hydration measurements obtained from nine subjects, based on pre- and post-treatment Novameter readings, are presented in Table 3 below. These measurements reveal a statistically significant increase in hydration of the skin post-treatment. Table 4 below presents measurements of skin extensibility and elasticity from nine subjects, obtained using a Cutometer. These measurements reveal a statistically significant increase in both extensibility and elasticity.

TABLE 2

ELASTICITY BY CUTOMETER

| SUBJ. INIT. | ID NO. | DISTENSIBILITY R0 PRE | DISTENSIBILITY R0 POST | GROSS ELASTICITY R2 PRE | GROSS ELASTICITY R2 POST | ELASTIC FUNCTION R5 PRE | ELASTIC FUNCTION R5 POST |
|---|---|---|---|---|---|---|---|
| AS | 1 | 0.440 | 0.540 | 0.568 | 0.556 | 0.548 | 0.475 |
| AS | 1 | 0.460 | 0.470 | 0.630 | 0.638 | 0.531 | 0.576 |
| ED | 2 | 0.330 | 0.380 | 0.636 | 0.579 | 0.478 | 0.519 |
| ED | 2 | 0.330 | 0.450 | 0.485 | 0.622 | 0.417 | 0.429 |
| MM | 3 | 0.460 | 0.360 | 0.674 | 0.694 | 0.472 | 0.640 |
| MM | 3 | 0.330 | 0.430 | 0.697 | 0.767 | 0.696 | 0.529 |
| DH | 4 | 0.320 | 0.370 | 0.844 | 0.757 | 0.720 | 0.500 |
| DH | 4 | 0.340 | 0.360 | 0.676 | 0.806 | 0.538 | 0.567 |
| JD | 5 | 0.300 | 0.360 | 0.467 | 0.583 | 0.250 | 0.423 |
| JD | 5 | 0.280 | 0.480 | 0.464 | 0.604 | 0.450 | 0.562 |
| HG | 6 | 0.210 | 0.230 | 0.571 | 0.478 | 0.533 | 0.600 |
| HG | 6 | 0.230 | 0.340 | 0.478 | 0.647 | 0.533 | 0.462 |
| RY | 7 | 0.300 | 0.320 | 0.600 | 0.594 | 0.565 | 0.609 |
| RY | 7 | 0.380 | 0.430 | 0.579 | 0.651 | 0.481 | 0.529 |
| SK | 8 | 0.240 | 0.280 | 0.583 | 0.786 | 0.389 | 0.652 |
| SK | 8 | 0.270 | 0.320 | 0.593 | 0.844 | 0.450 | 0.640 |
| AP | 9 | 0.600 | 0.610 | 0.450 | 0.672 | 0.186 | 0.574 |
| AP | 9 | 0.480 | 0.510 | 0.458 | 0.510 | 0.273 | 0.500 |
| MEAN> | | 0.350 | 0.402 | 0.581 | 0.655 | 0.473 | 0.544 |
| SD> | | 0.102 | 0.096 | 0.104 | 0.103 | 0.138 | 0.071 |
| Variance> | | 0.0104 | 0.0092 | 0.0109 | 0.0107 | 0.0190 | 0.0050 |
| Observations> | | 18 | 18 | 18 | 18 | 18 | 18 |
| Pearson Correlation> | | | 0.807 | | 0.496 | | 0.060 |
| df> | | | 17 | | 17 | | 17 |
| t Stat> | | | −3.586 | | −3.019 | | −1.992 |
| P(T<=t) one-tail> | | | 0.001 | | 0.004 | | 0.031 |
| t Critical one-tail> | | | 1.740 | | 1.740 | | 1.740 |
| P(T<=t) two-tail> | | | 0.002 | | 0.008 | | 0.063 |
| t Critical two-tail> | | | 2.110 | | 2.110 | | 2.110 |

TABLE 3

SKIN HYDRATION BEFORE AND AFTER TREATMENT

|  |  | HYDRATION (DPM) | |
|---|---|---|---|
| SUBJ. INIT. | ID NO. | PRE-TREATMENT | POST-TREATMENT |
| AS | 1 | 140 | 172 |
| ED | 2 | 119 | 139 |
| MM | 3 | 99 | 137 |
| DH | 4 | 111 | 111 |
| JD | 5 | 101 | 120 |
| HG | 6 | 115 | 167 |
| RY | 7 | 125 | 144 |
| SK | 8 | 104 | 126 |
| AP | 9 | 102 | 122 |
| MEAN > | | 113 | 138 |
| SD > | | 14 | 21 |
| Variance > | | 182 | 436 |
| Observations > | | 9 | 9 |
| Pearson Correlation > | | | 0.719 |
| df > | | | 8 |
| t Stat > | | | −5.0734 |
| P(T<=t) one-tail > | | | 0.0005 |
| t Critical one-tail > | | | 1.8595 |
| P(T<=t) two-tail > | | | 0.0010 |
| t Critical two-tail > | | | 2.3060 |

TABLE 4

REPLICA LINE ANALYSIS RAHU596

|  |  | NUMBER OF LINES | | MEAN LENGTH | | TOTAL LINE LENGTH | |
|---|---|---|---|---|---|---|---|
| SUBJ. INIT. | ID NO. | PRE TREATMENT | POST TREATMENT | PRE TREATMENT | POST TREATMENT | PRE TREATMENT | POST TREATMENT |
| AS | 1 | 308 | 277 | 0.553 | 0.531 | 170 | 147 |
| ED | 2 | 489 | 426 | 0.669 | 0.675 | 327 | 288 |
| MM | 3 | 402 | 384 | 0.895 | 0.741 | 360 | 284 |
| DH | 4 | 387 | 299 | 0.819 | 0.871 | 317 | 260 |
| JD | 5 | 387 | 414 | 0.927 | 0.863 | 359 | 357 |
| HG | 6 | 243 | 130 | 0.634 | 0.457 | 154 | 59 |
| RY | 7 | 411 | 234 | 0.713 | 0.535 | 293 | 125 |
| SK | 8 | 320 | 372 | 0.810 | 0.492 | 259 | 183 |
| MEAN> | | 368 | 317 | 0.753 | 0.646 | 280 | 213 |
| SD> | | 75 | 102 | 0.131 | 0.166 | 80 | 100 |
| Variance> | | 5699 | 103692 | 0.017 | 0.027 | 6401 | 10047 |
| Observations> | | 8 | 8 | 8 | 8 | 8 | 8 |
| Pearson Correlation> | | 0.679 | | 06876 | | 0.863 | |
| df> | | 7 | | 7 | | 7 | |
| t Stat> | | 1.937 | | 2.486 | | 3.717 | |
| P(T<=t) one-tail> | | 0.047 | | 0.021 | | 0.004 | |
| t Critical one-tail> | | 18950 | | 1.895 | | 1.895 | |
| P(T<=t) two-tail> | | 0.094 | | 0.042 | | 0.007 | |
| t Critical two-tail> | | 2.365 | | 2.365 | | 2.365 | |

EXAMPLES 3 and 4

Two well-known dermatologists having extensive experience in treating actinic keratoses conducted clinical tests using the method of the present invention. Both dermatologists live in extremely sunny areas, where the prevalence of keratoses is not only high, but also severe and extensive, with multiple lesions in all stages of development. These disseminate forms respond only partially or poorly to conventional treatments, such as 5-fluorouracil. Moreover, the conversion of squamous cell cancer is much greater than in other areas, with a potential for metastatic spread.

Both dermatologists were requested to pick extensive, severe cases of actinic keratoses which are resistant to other treatment. Each dermatologist followed our prescribed regimen of having the patient apply the tretinoin-containing solution to the entire face every other day for two weeks, increasing to daily applications for a total period of one month. The composition applied was a 0.25 percent by weight solution of tretinoin in a 50:50 mixture of 95% ethanol/polyethylene glycol 400.

Both dermatologists reported impressive results. After intensive inflammation during the treatment period, visible keratoses had largely disappeared within two weeks after the last treatment. So far, the follow-up period is too short to estimate the rate of recurrence. However, both dermatologists emphasized that the beneficial effects of tretinoin in removing actinic keratoses was far greater than could be achieved by twice daily applications of 5-fluorouracil for one month.

These results suggest that high strength tretinoin may also be effective in treating multiple basal and squamous cell tumors which develop on the photodamaged forearms of immunosuppressed patients who have received renal transplants. Myriads of warts also develop in these patients. One such patient has been treated for five weeks with a striking elimination of neoplastic growths.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

We claim:

1. A method for treating a skin disorder excluding acne, comprising topically applying to skin to be treated a retinoid-containing composition comprising a retinoid in a dermatologically acceptable vehicle, the concentration of retinoid in the composition and the topical application being effective to induce desquamation of the skin to ameliorate the disorder.

2. The method according to claim 1, wherein the composition contains greater than 0.1 weight percent tretinoin.

3. The method according to claim 1, wherein the composition contains at least about 0.2 weight percent tretinoin.

4. The method according to claim 1, wherein the composition is a solution of retinoid in a vehicle selected from the group consisting of ethanol, isopropanol, acetone, diethyl ether, propylene glycol, polyethylene glycol, and hydroalcoholic solvents.

5. The method according to claim 4, wherein the vehicle comprises a mixture of ethanol and polyethylene glycol.

6. The method according to claim 1, further comprising an agent for enhancing penetration of the retinoid into the skin to be treated.

7. The method according to claim 1, further comprising the step of allowing the applied composition to dry on the skin by at least partial evaporation of the vehicle.

8. The method according to claim 1, wherein the treated skin is human skin selected from the group consisting of facial skin, forearms, hands, upper chest, upper back, neck and scalp.

9. The method according to claim 1, wherein the skin to be treated is affected with a skin disorder selected from the group consisting of photodamaged skin, hyperpigmentation, rosacea, premalignant skin cancers, wrinkles, superficial scarring, epidermal atrophy and atypia, and keratosis pilaris.

10. The method according to claim 1, wherein the composition is initially applied to the skin on the average of from about every day for up to about one month to every other day for up to about two months.

11. The method according to claim 10, wherein after the initial application, treatment is treatment is tapered off to a lower concentration composition containing a retinoid for maintenance of the treated skin.

* * * * *

UNITED STATES PATENT AND TRADEMARK OFFICE
CERTIFICATE OF CORRECTION

PATENT NO.    : 6,228,887 B1                                           Page 1 of 1
DATED         : May 8, 2001
INVENTOR(S)   : Douglas E. Kligmann and Albert M. Kligman It is certified that error appears in the above-identified patent and that said Letters Patent is hereby corrected as shown below:

<u>Title page,</u>
Item [63], Related U.S. Application Data, should read as follows:
-- Continuation of application No. PCT/US98/09440, filed on May 11, 1998, and a continuation-in-part of application No. 09/071,017, filed on May 1, 1998, now Patent No. 6,008,254. --

<u>Column 1,</u>
Lines 10-11, after "Ser. No. 09/071,017," should read -- filed May 1, 1998, --

Signed and Sealed this

Fifth Day of February, 2002

Attest:

JAMES E. ROGAN
*Attesting Officer*    *Director of the United States Patent and Trademark Office*